United States Patent
Coloma González et al.

(10) Patent No.: US 10,829,444 B2
(45) Date of Patent: Nov. 10, 2020

(54) UREA FINISHING AND OFF-GAS TREATMENT PLANT AND PROCESS

(71) Applicant: STAMICARBON B.V., Sittard (NL)

(72) Inventors: Juan Coloma González, Maastricht (NL); Johannes Henricus Mennen, Meijel (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 16/472,792

(22) PCT Filed: Jul. 13, 2018

(86) PCT No.: PCT/NL2018/050484
§ 371 (c)(1),
(2) Date: Jun. 21, 2019

(87) PCT Pub. No.: WO2019/013639
PCT Pub. Date: Jan. 17, 2019

(65) Prior Publication Data
US 2020/0283377 A1    Sep. 10, 2020

(30) Foreign Application Priority Data

Jul. 14, 2017  (EP) .................................. 17181412

(51) Int. Cl.
| | | |
|---|---|---|
| C07C 273/16 | (2006.01) | |
| B01D 53/58 | (2006.01) | |
| B01D 53/73 | (2006.01) | |
| B01J 2/04 | (2006.01) | |
| B01J 4/00 | (2006.01) | |
| B01D 47/10 | (2006.01) | |

(52) U.S. Cl.
CPC ............ *C07C 273/16* (2013.01); *B01D 47/10* (2013.01); *B01D 53/58* (2013.01); *B01D 53/73* (2013.01); *B01J 2/04* (2013.01); *B01J 4/001* (2013.01); *B01D 2258/02* (2013.01)

(58) Field of Classification Search
CPC . C07C 273/16; C07C 273/189; C07C 273/02; C07C 273/04; B01D 53/73; B01D 53/58; B01D 47/10; B01D 2258/02; B01J 4/001; B01J 2/04
See application file for complete search history.

(56) References Cited

U.S. PATENT DOCUMENTS

| | | |
|---|---|---|
| 4,104,041 A | 8/1978 | Arita et al. |
| 4,153,431 A | 5/1979 | Higgins |
| 2011/0162350 A1 | 7/2011 | Ponnathpur |

FOREIGN PATENT DOCUMENTS

| | | |
|---|---|---|
| CN | 102844533 | 12/2012 |
| EP | 0 084 669 | 8/1983 |
| WO | WO-2015/002535 | 1/2015 |
| WO | WO-2017/007315 | 1/2017 |

OTHER PUBLICATIONS

International Preliminary Report on Patentability for PCT/NL2018/050484, dated Apr. 15, 2019, 7 pages.
International Search Report and Written Opinion for PCT/NL2018/050484, dated Oct. 17, 2018, 9 pages.

*Primary Examiner* — Jafar F Parsa
(74) *Attorney, Agent, or Firm* — Morrison & Foerster LLP

(57) ABSTRACT

The invention pertains to a finishing process for urea-comprising material, a plant for finishing urea-comprising material, a method of modifying an existing plant, and a use. Methods are disclosed for preventing the clogging of the conduit for off-gas between the finishing section and the treatment section.

21 Claims, 1 Drawing Sheet

UREA FINISHING AND OFF-GAS TREATMENT PLANT AND PROCESS

CROSS-REFERENCE TO RELATED APPLICATIONS

This application is the national phase of PCT application PCT/NL2018/050484 having an international filing date of 13 Jul. 2018, and published as WO 2019/013639 on 17 Jan. 2019, which claims benefit of European patent application No. 17181412.2 filed 14 Jul. 2017. The contents of the above patent applications are incorporated by reference herein in their entirety.

FIELD OF THE INVENTION

The invention relates to the production of urea and urea-containing fertilizers, especially to urea finishing. In particular, the invention relates to the transport of off-gas (i.e. exhaust air comprising urea and ammonia) from a finishing section to an off-gas treatment section. The treatment section is e.g. for dust scrubbing and/or acid scrubbing to remove urea and/or ammonia from the off-gas. In the finishing section typically a urea-containing melt is solidified to produce e.g. urea particles, urea ammonium nitrate (UAN) particles or urea ammonium sulphate (UAS) particles.

BACKGROUND

Urea plants frequently comprise a finishing section for solidification of a urea-containing liquid stream (e.g. urea melt) into a solid urea-containing product. Common finishing sections are prilling towers and granulators. Prilling towers and granulators use cooling air and therefore yield as off-gas an air stream which is contaminated with urea-containing dust and ammonia. The urea dust often includes submicron particles containing for instance, urea, UAS or UAN. This off-gas needs to be treated to remove the major part (or even essentially all) of the solids and ammonia before the treated off-gas stream (cleaned air stream) is vented into the atmosphere. The off-gas treatment is generally necessary to comply with environmental regulations which limit the allowed urea and ammonia emissions. It is also economically desirable to recover components from the gas stream, such as urea and ammonia. This increases the efficiency of the plant.

The removal of urea dust is challenging per se, since the amounts of off-gas (mainly air) are enormous, whilst the concentration of urea dust is low. An example indicative air flow for a relatively small urea prilling tower of ca. 1500 metric ton per day is 500 000 $Nm^3/hr$. A larger urea prilling tower may for instance have an air flow of $1.0 \times 10^6$ $Nm^3/hr$, for instance with a urea capacity of about 2500 metric ton per day, or even higher. A typical concentration of urea dust therein is about 0.02 wt. %. Further, part of the urea dust is of a submicron size. Satisfying current standards implies the need to remove a major part of this submicron urea dust.

A prilling tower can for instance have a height of for example 60 m to 80 m. Smaller plants may have a free fall path of 50 m or less. Some of the largest plants have prilling towers of 125 m height. Urea dust emissions of more than 200 $mg/Nm^e$ have been reported for some existing urea prilling towers.

Older prilling towers frequently vent off-gas directly to the atmosphere without any dust or ammonia abatement. The tower construction generally sets a maximum available space on its top and a maximum additional weight that can be supported by its structure and therefore the design of any abatement systems installed on top as part of revamping is limited. Existing emission abatement technologies typically require large and heavy fans or pumps to overcome the additional pressure drop that they require. The larger the efficiency of the dust capture, the larger the pressure drop required, especially when dealing with submicron particle removal. Many off-gas treatment systems are not suitable for installation on top of an existing prilling tower because of their weight, but can be installed at or near ground level (e.g. with the inlet at 0 to 20 m elevation). This may involve first bringing the off-gas to a lower elevation through a conduit (e.g. duct), and hence also the construction of a duct from the top of the urea prilling tower to about ground level. The duct is generally arranged outside the prilling tower.

The off-gas treatment is generally carried out in a separate treatment section (emission abatement section), which has an inlet for the off-gas connected by a conduit coming from the urea finishing section. Generally, a connecting conduit can have a wall that is for a major part exposed to the outside environment. This environment can have low temperatures, such as below 0° C. or below −10° C., e.g. overnight or in winter.

The off-gas treatment typically comprises scrubbing with aqueous solutions to remove dust (scrubbing), or scrubbing the gas stream with an acid solution to remove ammonia by conversion to ammonium salts (acid scrubbing), or both in series or simultaneously. If both dust scrubbing and acid scrubbing are used in series, dust scrubbing is typically done first. If they are done simultaneously, urea is combined with ammonium salts like UAS and UAN. In a scrubber, a scrubbing liquid (for instance a solution) is sprayed into the gas stream in e.g. co-current and/or counter current flow. The scrubbing solution is typically circulated so as to have a desired concentration of urea. A purge stream is removed from the scrubber and disposed of, e.g. in case of dust scrubbing with water, by recycling to the urea plant for recovery of urea.

Typically, remaining scrubbing droplets are removed from the gas stream in a treatment section using e.g. a mist eliminator. Sometimes, a combination of equipment of different working principles is necessary to achieve sufficient cleaning of the off-gas treatment section so as to comply with emission regulations. Examples of other types of abatement equipment are the wet electrostatic precipitator, and the Venturi scrubbers. As a result, the necessary equipment will have a certain weight and size.

In some off-gas treatment sections, a quenching step is applied prior to the scrubbing, e.g. spraying aqueous solution in such a way as to cause evaporative cooling, so as to reduce the size of the gas stream and so as to allow for smaller equipment in the downstream treatment steps such as scrubbing. Furthermore, WO 2015/002535 and US 2016/0184758 describe a method for the removal of urea dust from the off-gas of a finishing section of a urea production plant, the method comprising subjecting the off-gas to quenching with water so as to produce quenched off-gas having a temperature below about 45° C., and subjecting the quenched off-gas to scrubbing using at least one Venturi scrubber The present invention relates to the transport of the off-gas from the urea finishing section to an off-gas treatment section. The off-gas is generally carried through a conduit between the urea finishing section and the off-gas treatment section.

Generally, and also in the present invention, the conduit is e.g. a tube, pipe or duct, or any other kind of gas transport system. The conduit generally comprises a wall and a gas flow pathway. The conduit can have a length of e.g. at least 2 m, at least 5 m, at least 10 m, at least 20 m or at least 40 m.

For instance, a prilling tower can have the off-gas outlet at a height of at least 10 m, at least 20 m, at least 40 or at least 60 m, above ground level, namely at the top of the tower. Although some small-size off-gas treatment sections can sometimes be placed on top of a urea prilling tower, many larger off-gas treatment sections need to be placed on ground level due to the weight and/or size of the equipment, and have an inlet e.g. at 0 to 5 m above ground level. This necessitates a corresponding length of the conduit, e.g. at least 10 m, at least 20 m, at least 30 m, at least 40 or at least 60 m. Also with other types of urea finishing sections and off-gas treatment sections, a certain minimum length of the conduit can be given by design constraints of the plant. A minimum length of the conduit can also be the case if e.g. an existing urea plant is modified in a so-called revamping.

Furthermore it is known that at higher temperatures, e.g. above 60° C., pure solid urea has a tendency to cake, i.e. to agglomerate and form lumps. Hence, any urea dust that settles in conduits is at risk of caking at higher temperatures, especially when exposed to moisture such as air humidity.

A problem in conduits for transporting off-gas from urea finishing section to a treatment section is that after some operating time of the off-gas treatment section, an increased pressure drop tends to occur. This can lead to higher operating costs and/or reduced throughput of the off-gas treatment section. This pressure drop increase is frequently caused by clogging of the conduit (e.g. duct) between the finishing section and off-gas treatment section. This clogging is caused by solid deposits in the conduit. The solid deposits comprise urea, e.g. solid urea material which forms on at least part of the walls of the conduit. The clogging causes an increase of the pressure drop that can block the operation or require additional energy consumption of extraction fans or pumps (in case of Venturi tubes or Venturi ejectors) for transporting the off-gas to the treatment section.

Some prior art deals with plugging of a scrubber for treating urea finishing off-gas. EP 0084669 mentions that nozzles for spraying liquid into the gas stream become plugged. In order to address this, formaldehyde is added to the washing solution. However, formaldehyde is toxic and expensive and is therefore highly undesirable in an off-gas treatment section which aims for yielding a clean air stream to be vented in the atmosphere. U.S. Pat. No. 4,104,041 describes a urea prilling off-gas treatment process wherein a liquid film of scrubbing solution is formed traverse across the whole passage, so as to remove urea dust with about 1 μm particle size. This is said to solve the problem of pore clogging of prior art bag filters. U.S. Pat. No. 4,153,431 also refers to the problem of clogging of prior art filters, which causes increased pressure drop which is identified as major disadvantage for natural draft and forced draft urea prilling towers. A process comprising directing a scrubbing liquid against a filter co-current with the flow of the gas is described. EP 0084669, U.S. Pat. Nos. 4,104,041, and 4,153,431 do not deal with urea deposits in conduits between the finishing section and off-gas treatment section, but rather with urea deposits inside the respective treatment sections.

SUMMARY

The invention pertains in a first aspect to a finishing process for urea-comprising material comprising:

subjecting a urea-comprising liquid stream to solidification in a urea finishing section, yielding a solid urea-comprising product and an off-gas stream comprising air, urea dust and ammonia, transporting said off-gas stream from an outlet of said urea finishing section to an off-gas treatment section through a conduit having a wall, wherein said off-gas has a temperature $T_1$ at said outlet, subjecting said off-gas stream to a treatment to remove at least part of said urea dust and/or ammonia from said air in said treatment section, and maintaining a temperature of said wall of said conduit higher than $T_1 - 50°$ C. in at least one bend of the conduit, in at least one section where the diameter of the conduit changes and/or over at least 10%, at least 50% or at least 90% of the length of the conduit.

The invention also pertains to a plant for finishing urea-comprising material, wherein the plant comprises a finishing section for solidifying a urea-containing liquid stream, an off-gas treatment section, and a conduit for off-gas from an outlet of said finishing section to an inlet of said treatment section, wherein said conduit comprises a wall, and wherein at least parts or all of said conduit are provided with thermal insulation and/or with one or more heating elements for maintaining a minimum temperature of said wall.

The invention also pertains to the use of heat tracing for preventing clogging of a conduit for a gas stream comprising urea-comprising dust, ammonia, and isocyanic acid.

The invention also pertains to a method of modifying an existing finishing section for solidifying urea-containing material, for avoiding clogging in a conduit having a wall for off-gas from the finishing section, wherein said conduit is provided between said finishing section and a treatment section for treating off-gas from said finishing section, the method comprising providing the conduit with thermal insulation and/or with one or more heating elements for avoiding cold spots of said wall of said conduit.

DETAILED DESCRIPTION

The present invention is in some embodiments based on the judicious insight that urea deposits in the conduit between the finishing section and off-gas treatment section can be avoided by preventing cold spots in the conduit wall. Hence, the urea deposits can be addressed e.g. by heating and/or thermally insulating the conduit wall or at least parts thereof.

Without wishing to be bound by way of theory, the initial build-up of solid urea in the conduit, e.g. duct, especially on the inner wall surface of the conduit exposed to the off-gas stream, is believed to be caused by the condensation and adhesion of at least some of the isocyanic acid present in the off-gas stream and the back-conversion of isocyanic acid to urea by reaction with $NH_3$.

Isocyanic acid (HNCO) results from the thermal decomposition of ammonium cyanate (NH$_4$NCO). Ammonium cyanate is in chemical equilibrium with urea (NH$_2$CONH$_2$):

$$NH_2CONH_2 \leftrightarrow NH_4NCO \leftrightarrow HNCO + NH_3 \quad (1)$$

(urea↔ammonium cyanate↔isocyanate+ammonia)

The decomposition of ammonium cyanate to isocyanic acid and ammonia is promoted by low pressure and high temperatures, such as when a urea solution is concentrated for solidification, for instance during a prilling operation. The reaction products volatilize into the off-gas. Hence, the off-gas contains e.g. at least 10 mg NH$_3$/Nm$^3$ or at least 50 mg NH$_3$/Nm$^3$ or at least 100 mg NH$_3$/Nm$^3$. The off-gas contains e.g. at least 10 mg dust/Nm$^3$ or at least 50 mg dust/Nm$^3$ or at least 100 mg dust/Nm$^3$, and preferably such amounts of urea-containing dust. Preferably the off-gas comprises at least 10 mg NH$_3$/Nm$^3$ or at least 50 mg NH$_3$/Nm$^3$ or at least 100 mg NH$_3$/Nm$^3$ urea. The off-gas contains e.g. at least 5.0 mg isocyanic acid/Nm$^3$ or at least 10 mg isocyanic acid/Nm$^3$ or at least 50 mg isocyanic acid/Nm$^3$ The reverse reaction can take place in the conduit, when isocyanic acid condenses at cold spots of the wall of the conduit and reacts with ammonia which is also present in the off-gas stream to form urea. The reaction of the isocyanic acid with ammonia may occur prior to, simultaneously with, or subsequently to the condensation.

Figure 1:
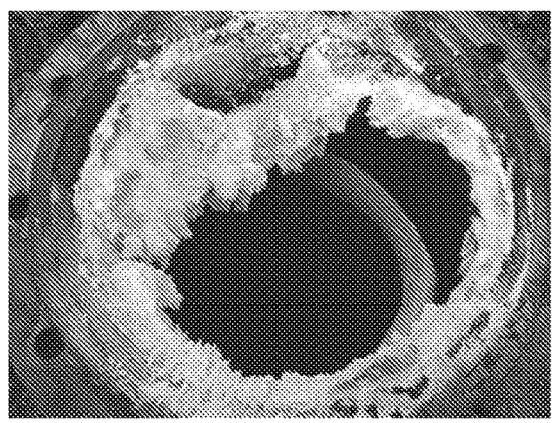
FIG. 1 is a photograph of solid material adhered to the inner wall in a comparative conduit between a finishing section and a treatment section.

Formed urea particles can be dragged by the air stream and are expected to be small in size due to the chemical nature of its formation mechanism, for instance below 1 μm. However the reaction with ammonia can also occur on the wall and result in adhesion of solids. Ultimately, this yields urea accumulation on the wall of the conduit, in particular in the build-up of large clogs or clumps of solid materials, for example as illustrated in FIG. 1.

By avoiding cold spots on the wall of the conduit, e.g. by insulating and/or heating the conduit, or at least parts of the walls thereof, for example using tracing as heating elements, the problem of the urea deposits is solved, hence by avoiding cold spots on the internal wall of the conduit. Advantageously, the operational time of the finishing plant (finishing section and treatment section) is increased because the downtime for maintenance and cleaning is reduced. Advantageously, as it is not necessary to use water or steam for rinsing the conduit, operation is simple and no additional flushing systems are necessary. A further advantage is that it is not necessary to add additives such as formaldehyde into the process streams for preventing clogging.

Furthermore, advantageously the amount of submicron urea particles at the inlet of the treatment section may be reduced.

Generally, the invention can be applied for instance in a finishing section and/or off-gas treatment section of the types as described above.

Accordingly, the invention in an aspect relates to a urea finishing process. As used herein, urea finishing refers to a process for solidification of a urea-containing solution, in particular a urea-containing melt. Examples include a melt of urea, urea ammonium nitrate (UAN) and urea ammonium sulphate (UAS). Examples of urea finishing processes include granulation and prilling of urea, UAN and UAS. The melt typically comprises less than 5 wt. % water and typically more than 50 wt. % urea.

The process in an embodiment comprises subjecting a urea-comprising liquid stream to solidification in a urea finishing section. This yields a solid urea-comprising product and an off-gas stream comprising ammonia and dust particles comprising urea. The off-gas stream further comprises air, and (small amounts of) biuret and isocyanic acid, as well as formaldehyde in case of granulation. The process further comprises transporting said off-gas stream from an outlet of said urea finishing section to an off-gas treatment section through a conduit having a wall, for instance through a duct. Preferably the transporting involves forced draft, e.g. using a blower or fan. The off-gas has a temperature T$_1$ at said outlet. The temperature T$_1$ is the average temperature over the cross-section of the outlet. The process further comprises subjecting said off-gas stream to a treatment, for cleaning said off-gas at least partially, for instance to remove at least part of said urea containing dust and/or ammonia in said treatment section.

In some embodiments, the finishing section, solidification step, treatment step, and/or treatment section are for example as described in the introduction part of the present application.

The finishing section is for example a prilling tower or a granulator. The invention is particularly advantageous for prilling towers. The prilling tower is for example of the forced draft, or natural draft type. The granulator is for example a fluidized bed granulator, spouted bed granulator, a pan granulator, or a drum granulator. Fluidized bed and spouted bed granulators are preferred and use air streams. The solidification step for example comprises prilling in a prilling tower or granulation in a granulator. The solidification involves removal of the heat of crystallization, and typically also sub-cooling of the solidified urea product. The solidification comprises for instance cooling of droplets of the urea-comprising liquid using cooling air. Usually most of the crystallization/cooling heat is removed by air cooling. For instance 3-30 kg of air per kg of final solidified product is used for cooling, preferably 5-15 kg. Optionally the solidification involves granulation and a part of the heat is removed by evaporation of water. The cooling air, by nature of the cooling process, leaves the finishing section as off-gas at an increased temperature. In the finishing section, the air comes into direct contact with the urea melt and with the solidified urea particles. This leads to some contamination of the air with some urea dust and ammonia. Depending on the type and operation conditions of the finishing section, the amount of dust present in the gas stream at the outlet of the finishing section, before any scrubbing, is e.g. 0.01-1.0 wt. % (based on gas stream mass). The typical temperature of the off-gas exiting a finishing section of a urea plant, i.e. at the outlet, is e.g. at least 30° C., at least 50° C., at least 70° C., such at least 80° C., at least 90° C., at least 100° C., and typically less than 150° C., less than 140° C., or less than 120° C. For granulation, especially fluid bed granulation, the temperature is e.g. 70-150° C., or 80-140° C., such as about 105° C.

The urea-comprising liquid is for instance a urea comprising solution or melt, with e.g. at least 80 wt. %, at least 90 wt. %, or at least 95 wt. % urea. The liquid may for instance also be a solution and/or melt of e.g. urea ammonium nitrate (UAN) or urea ammonium sulfate (UAS). Fluidized bed granulation of UAS is mentioned for instance in WO 2017/007315.

In a further embodiment, the liquid may for example also comprises small amounts of ammonium salts such as ammonium nitrate and/or ammonium sulfate, such as up to 1 wt. % or up to 5 wt. %, e.g. for disposal of salts from acid scrubbing of the off-gas. The liquid may also comprise additives such as formaldehyde. The liquid comprises typically less than less than 5 wt. % water, for instance less than 2.0 wt. % water for granulation and typically less than 0.50 wt. % water for prilling.

The treatment section and off-gas treatment step typically involves dust scrubbing and/or acid scrubbing. The scrubbing generally involves contacting the gas stream with an aqueous solution, e.g. comprising urea, for instance by spraying the solution into the off-gas stream. The solution has for instance neutral pH (pH 6-8, e.g. pH 7) for dust scrubbing to remove urea dust, or low pH (pH lower than 4 or lower than 3) for acid scrubbing. If dust scrubbing and acid scrubbing are combined, acid scrubbing is applied for instance simultaneously with or downstream of dust scrubbing. Dust scrubbing generally involves recirculating a scrubbing solution from which a purge stream comprising e.g. 10-60 wt. % urea is withdrawn. The purge stream is disposed of, e.g. concentrated by water evaporation and returned to the finishing section.

The treatment section can have many designs but typically comprises a droplet removal device such as meshes and Chevron demisters. The treatment section can also contain a Venturi scrubber. A Venturi scrubber, for instance as described in WO 2015/002535, comprises one or more tubes with a converging part, a narrow or "throat" part, and typically a diverging part. As the air moves through the throat it is accelerated to a high velocity. A scrubbing fluid in the form of droplets, typically an aqueous solution, is added to the Venturi, usually at the throat, and enters the gas flow. The water droplets used are generally many orders of magnitude larger than the contaminant particles (urea dust) to be collected and, as a consequence, accelerate at a different rate through the Venturi. The differential acceleration causes interactions between the water droplets and the contaminant particles, such that the contaminant particles are collected by the water droplets.

In an example embodiment, the dust removal system comprises a plurality of Venturi ejectors operated in parallel. For instance a MMV-section (micro-mist Venturi) can be used, especially, for granulation) can be used. The MMV-section comprises multiple parallel Venturi tubes. In the MMV-section liquid is sprayed in the throat of each Venturi tube co-current with the gas-flow through single phase nozzles e.g. arranged directly upstream the converging tube part, creating a consistent and adjustable liquid droplet-size, typically in a range of from 50 µm to 700 µm. Optionally throat spray counter-currently with the gas-flow is used to control the pressure drop over the Venturi-section, e.g. with nozzles inside the throat.

In an embodiment, a treatment step comprises subjecting the off-gas to quenching with water so as to produce quenched off-gas for instance having a temperature below about 45° C., and subjecting the quenched off-gas to scrubbing. The scrubbing step for example uses at least one Venturi scrubber.

The treatment step comprises for instance subjecting the off-gas stream to a cooling step, such as a quenching step, e.g. to a temperature below 45° C. or below 40° C., and/or cooling by e.g. at least 50° C. or at least 60° C. The cooling is for instance by spraying and evaporation of an aqueous stream, such as a urea solution, e.g. by evaporating at least 1.0 g, at least 10 g, or at least 20 g water per Nm$^3$ off-gas. The gas stream after the cooling has for instance at least 70% or at least 80% relative humidity (RH). The spraying results for example in droplets having average droplet size of less than 100 µm, less than 40 µm or less than 20 µm. Preferably, co-current spraying is used for the quenching.

The conduit between the finishing section and off-gas treatment section comprises e.g. piping, a tube, and/or a duct. More generally, any gas flow transport line can be used. The conduit has a wall that acts as a gas impermeable boundary with the outside atmosphere. The conduit has a length of for instance at least 2 m, at least 5 m, at least 10 m, at least 20 m, at least 40 m, or at least 60 m. The conduit runs for instance from the top of a urea prilling tower to a lower level, e.g. to a treatment section placed at less elevation, such as placed at ground level or having an inlet at 0-20 m elevation, and/or a treatment section with an elevation that is lower than that of the off-gas outlet by at least 5 m, at least 10 m, at least 20 m, or at least 40 m.

The present invention generally aims at preventing cold spots on this wall.

Features A-F

Accordingly, the following measures A to F can be applied, each individually and/or in combination with each other.

A) The process can comprise maintaining the wall at a temperature not more than 60° C. lower than the temperature $T_1$ of the gas stream at the outlet of the finishing equipment. Hence, the process can comprise maintaining a wall temperature $T_w$ that is equal to or higher than $T_{w,min}$, wherein $T_{w,min}=(T_1-60°$ C.), or wherein $T_{w,min}=(T_1-50°$ C.), or wherein $T_{w,min}=(T_1-30°$ C.), or wherein $T_{w,min}=(T_1-10°$ C.), or even wherein $T_{w,min}=T_1$. In the latter case, $T_w \geq T_1$. Such wall temperatures $T_w$ are maintained typically in at least one bend of the conduit, in at least one section where the diameter of the conduit changes and/or over at least 10%, at least 50% or at least 90% of the length of the conduit. The wall temperature ($T_w$) refers to the temperature at the inner side of the wall (i.e. the temperature at the inner wall, that is at the surface of the wall that is in contact with the off-gas).

B) The process can comprise maintaining the wall at a temperature of at least 30° C., at least 40° C., at least 60 CC, at least 80° C., at least 100° C., or at least 120° C. Such wall temperatures are maintained typically in at least one bend of the conduit, in at least one section where the diameter of the conduit changes and/or over at least 10%, at least 50% or at least 90% of the length of the conduit. The wall temperature refers to the temperature at the inner side of the wall (at the surface of the wall that is in contact with the off-gas).

C) The temperature of the off-gas stream near the wall, e.g. in a zone less than 2 cm or less than 1 cm from said wall (internal surface, i.e. the surface exposed to the off-gas), is preferably higher than 60° C., preferably higher than 65° C., even more preferably higher than 70° C. Hence, the temperature of the gas stream near the wall has such a preferred temperature, for at least one position in the length of the conduit (e.g. along the gas flow), typically in at least one bend of the conduit, in at least one section where the diameter of the conduit changes and/or over at least 10%, at least 50% or at least 90% of the length of the conduit.

D) The difference in temperature between the gas stream near the wall of the duct, (e.g. in a zone less than 2 cm or less than 1 cm from said wall internal surface) and the gas stream in the centre of the cross-section of the conduit, at the same position over the length of the conduit, is preferably less than 10° C., more preferably less than 5° C., even more preferably less than 3° C. Hence, the temperature differences of the gas stream in the transversal cross-section (perpendicular to the flow of the gas) are preferably small.

E) Preferably, the process comprises heating of at least a part of the wall of the conduit. The heating can be applied for instance over at least 10%, at least 20%, at least 50% or at least 90% of the length (e.g. along the gas flow) of the conduit, and/or to at least 10%, at least 20%, at least 50% or at least 90% of the surface of the wall, e.g. of the outer surface of the wall. The heating can also be applied to the entire wall. The heating can be applied e.g. by electric heating and/or with a heating fluid, such as by direct or indirect heat exchange. The heating fluid is preferably steam or condensate. The steam can for instance in some embodiments be low pressure steam supplied from a high pressure carbamate condenser of the urea plant. Preferably heat tracing is applied to the wall for the conduit, e.g. electrical tracing and/or heating fluid tracing such as a steam jacket.

F) Thermal insulation materials can be applied, as described hereinafter. These features A-F can be used individually or in any combination. The same applies for the preferred sub-features. Some example combinations are features A and B; A, B, and E and/or F; C and E; D and E; C and D and optionally E; and B and E.

The above measures are particularly advantageous for a process comprising prilling urea-containing solid particles in a prilling tower, the tower having an outlet for cooling air as off-gas at the top (e.g. above the spraying device of the prilling tower), wherein said off-gas has a temperature $T_1$ at said outlet, and wherein the process comprises subjecting said off-gas to treatment, preferably dust scrubbing and optionally acid scrubbing in an off-gas treatment section, e.g. placed at ground level (such as at less than 20 m elevation), wherein said treatment section has an inlet for off-gas at ground level (e.g. 0 to 20 m or 0 to 10 m elevation). The process furthermore comprises bringing the off-gas stream from said outlet at said top of the urea prilling tower, through a conduit positioned outside the prilling tower, to said inlet of the treatment section. The treatment section preferably comprises a venturi scrubber and e.g. a quench sprayer as described.

A preferred urea finishing process comprises:
prilling urea in a urea prilling tower using cooling air, preferably with forced draft using a blower or fan, wherein the prilling tower has an outlet for off-gas at the top of said tower, wherein said off-gas has a temperature $T_1$ at said outlet,
subjecting said off-gas to dust scrubbing and optionally to acid scrubbing in an off-gas treatment section having an inlet for off-gas at 0 to 20 m elevation above ground level,
supplying off-gas from said outlet at said top of the urea prilling tower to said inlet of said off-gas treatment section, and
maintaining a temperature of said wall of said conduit higher than $T_1-10°$ C.

The invention also pertains to a plant for finishing urea-comprising material. The plant for finishing urea-comprising material comprises a finishing section for solidifying a urea-containing liquid stream (such as granulator or prilling tower), and an off-gas treatment section. The plant for finishing urea-comprising material also comprises a conduit for off-gas from an outlet for off-gas of the finishing section to an inlet for off-gas of the said treatment section. In a particular embodiment, the finishing section is a urea prilling tower, and/or the treatment section is placed 0 to 20 m elevation, e.g. at ground level.

At least parts of the conduit are provided with thermal insulation and/or with one or more heating elements, preferably with both thermal insulation and heating elements. Preferably, the plant is configured for carrying out the process as described. Preferably, the thermal insulation and the one or more heating elements, if used, are configured (each separately or together) for maintaining a temperature of said wall of said conduit higher than $T_{w,min}$, in at least one bend of the conduit, in at least one section where the diameter of the conduit changes and/or over at least 10%, at least 50% or at least 90% of the length of the conduit, wherein $T_w,min=T_1-50°$ C., wherein $T_1$ is the temperature of said off-gas at said outlet, even more preferably for a Tw,min as described.

The heating elements for instance serve as external heat source or provide heat from an external heat source. The insulation and/or one or more heating elements are configured for maintaining a minimum temperature of the wall of the conduit. The heating elements are for instance electrical heating elements, or heat exchangers for heat exchange with a heating fluid such as steam or condensate. The heating elements are for instance provided as trace heating. Electrical trace heating elements are for instance provided as electrical heating elements in physical contact along the length of a pipe, for example as heat tracing tape. Heating fluid trace heating elements are for instance provided as conduits for heating fluid in physical contact with the conduit over the length of the conduit.

Heat tracing tape comprises electric wires for instance encased in a polymer tape. The conduit is for example provided with self-regulating heat tracing tape, whose electrical resistance varies with temperature. Such tape comprise for instance cables comprising two parallel bus wires encased in a semi-conducting polymer loaded with carbon.

For instance, the conduit is provided with heat tracing, such as electric tracing and/or heating fluid tracing, over at least part or all of the length of the conduit (in the direction of the gas flow), such as over at least 1 m length, at least 2 m length, or at least 5 m lengths, or the entire length, in at least one bend of the conduit and/or at least section of the conduit where the diameter of the conduit decreases. Preferably the conduit has a perimeter and the insulation and/or one or more heating elements are provided, e.g. in such length parts, over at least 10%, at least 20%, at least 50%, or even at least 90% of the perimeter of the conduit.

Preferably, the thermal insulation material has a thickness of at least 1.0 mm, at least 5 mm, at least 10 mm, at least 5 cm or at least 10 cm, e.g. 5 to 15 cm. Preferably, the thermal insulation material is porous and/or comprises fibres. For example, the material comprises a foam material. Preferably, the thermal insulation material comprises voids filled with air, and has a void volume fraction of at least 10%, at least 20% or at least 50%. Preferably, the thermal insulation material comprises one or more materials selected from the group of a polymeric material, a fibre based material, and an inorganic non-metal material. Preferably the material is a glass based material, such as fiberglass. The thermal insulation material for instance has a thermal conductivity of less than 1.0 or less than 0.20 or less than 0.10 W m$^{-1}$K$^{-1}$(W/(m·K)), at 1 bar and 293 K; and preferably has a thickness as mentioned. Preferably, the material is applied over at least 0.50 m$^2$, at least 1.0 m$^2$, at least 5 m$^2$ or at least 10 m$^2$.

Preferably, the plant comprises a forced air prilling towers wherein e.g. a fan or a blower is used. In such a plant, the reduced pressure caused by a blower may induce more formation of isocyanic acid and hence more potential clogging. This can in particular be the case if the addition of a treatment section to an existing finishing section necessitates the installation of a blower or fan in or downstream of the finishing section.

The invention also provides a method of modifying an existing finishing section for solidifying urea-containing material (e.g. a urea finishing section), wherein the modification is for the purpose of avoiding, or at least reducing, clogging in the conduit. Hence, the revamping is carried out at least in part for avoiding (such as preventing or reducing) clogging of the conduit, wherein said conduit is provided between the finishing section and a treatment section for treating off-gas from said finishing section. Accordingly, the conduit is part of the existing urea finishing section, or is added to the existing urea finishing section. For instance, the method may comprise installing a treatment section, such as a replacement treatment section, additional treatment section, and/or new treatment section for a finishing section not yet having a treatment section. With such installation of the treatment section, the inlet for off-gas thereof is connected with an additional conduit to an outlet of the finishing section. In the method of the invention, the existing or new conduit is provided with thermal insulation and/or with heating elements. Preferably, the thermal insulation and/or one or more heating elements are provided for avoiding cold spots in the wall of the conduit. Accordingly, the thermal insulation and/or one or more heating elements are configured for avoiding cold spots. The cold spots are for instance located at the internal surface of the wall, i.e. the wall surface parts in contact with the off-gas stream. Cold spots include spots having a temperature so as to allow condensation of isocyanate. In the present method, colds spots of the internal wall are avoided. Cold spots generally have a temperature lower than the off-gas temperature. It is not necessary that cold spots are always present in the absence of the thermal insulation and/or heating elements. For instance cold spots can form during night or winter and not during days or not during summer. Typically, cold spots are spots of the wall (internal surface) that are colder than the off-gas during at least 10% of the operating time. The thermal insulation material is preferably as described for the plant. The added thermal insulation and/or one or more heating elements (if used) are adapted for reducing clogging of the conduit by avoiding such cold spots.

Preferably, the added thermal insulation and/or the one or more added heating elements are configured (if used) for maintaining a temperature of said wall of said conduit higher than $T_{w,min}$, in at least one bend of the conduit, in at least one section where the diameter of the conduit changes and/or over at least 10%, at least 50% or at least 90% of the length of the conduit, wherein $T_{w,min}=T_1-50°$ C., wherein $T_1$ is the temperature of said off-gas at said outlet, more preferably for a Tw,min as described herein.

Alternatively and/or in combination, a method of modifying an existing urea finishing section for avoiding clogging in a conduit having a wall for off-gas from the finishing section, comprises providing a conduit between said finishing section and a treatment section for treating off-gas from said finishing section, wherein the length of the conduit is less than 10 m, less than 5 m, or even less than 2.0 m. This length is used for the purpose of reducing the risk of clogging of the conduit, and in particular for reducing the risk of isocyanate condensation and urea back reaction on the internal surface of the wall of the conduit. Preferably, the inlet of the treatment section is placed on about the same elevation (e.g. at most 5 m lower or higher, or at most 2 m lower or higher) as the outlet for off-gas of the finishing section. For instance, the treatment section is placed on top of a urea prilling tower. Preferably, the conduit having such short conduit length is provided with thermal insulation material and/or one or more heating elements, such as heat tracing tape as described above.

The process is preferably carried out in a plant as described. The plant is preferably suitable for a process as described. The method of modifying an existing urea finishing section preferably results in a plant as described. The plant can be built as grass-roots plant (i.e. newly built) or by modifying or revamping an existing urea finishing plant.

The invention further pertains to use of heat tracing (such as electric tracing and/or heat fluid tracing) for preventing clogging of a conduit for a gas stream comprising urea-comprising dust, ammonia, and isocyanic acid.

The invention further pertains to a method of reducing clogging of a conduit for a gas stream comprising urea-comprising dust, ammonia, and isocyanic acid, wherein the conduit has a wall, wherein the method comprises applying one or more of said features A-F, and providing the gas stream to the inlet of the conduit and withdrawing the gas stream at the outlet of the conduit.

The source of the gas stream can be any source, typically a source in a plant wherein urea is produced. The conduit can be e.g. to a vent, stack or to treatment section, e.g. as described.

The gas stream comprises for instance at least 10 mg isocyanic acid/Nm$^3$, or at least 20 mg, or at least 50 mg, or at least 100 mg isocyanic acid, at the beginning of the conduit and also at the end of the conduit. Preferably, the concentration isocyanic acid at the outlet of the conduit is at least 80%, or at least 90%, or even at least 99% of the concentration at the inlet of the conduit.

The gas stream comprises for instance at least 10 mg $NH_3/Nm^a$, or at least 20 mg, or at least 50 mg, or even at least 100 mg $NH_3/Nm^3$ at the inlet of the conduit and typically also at the outlet of the conduit. The conduit is for instance a tube, pipe, or duct.

Embodiments of the invention will now be further illustrated in the following figures and example(s), which do not limit the invention or claims.

FIG. 1 shows deposits in a comparative conduit between a finishing section and a treatment section, observed after 10 days of continuous operation of pilot plant. The conduit was not thermally insulated or heated. A solid is formed in all the perimeter of the duct and is attributed to condensation and crystal growth.

Figure 2:
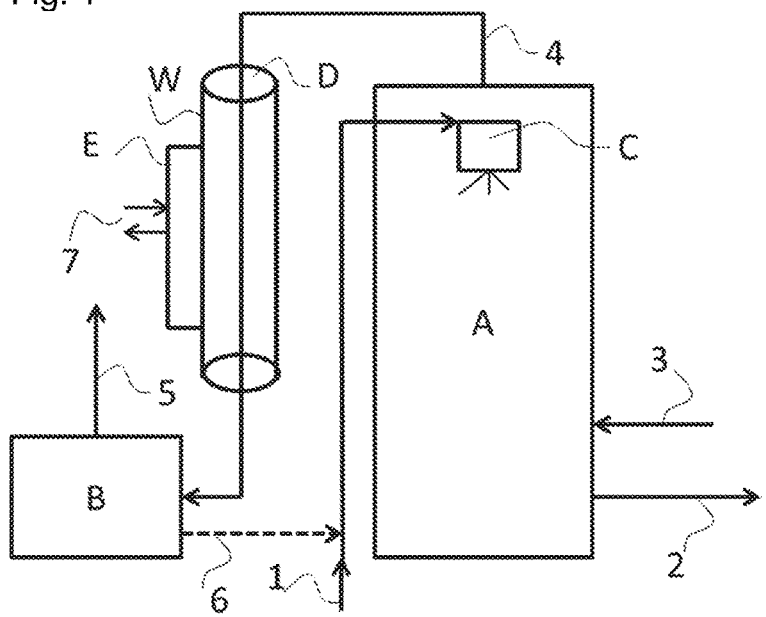
FIG. 2 schematically illustrates a process and urea finishing plant according to an embodiment of the invention.

FIG. 2 schematically illustrates an example embodiment of the invention, comprising a urea prilling tower A and a treatment section B (for dust and/or acid scrubbing) placed at ground level. Urea melt 1 is supplied to the top of the prilling tower A, and more in particular to the spraying device, e.g. a prilling bucket C. From spraying device, e.g. a prilling bucket C, the urea melt falls down inside the tower A, cools, crystallizes and solidifies into solid urea particles 2, using cooling air 3 and also giving off-gas 4. Off-gas 4 is supplied from the outlet of prilling tower A at the top of the tower to the scrubbing unit B through a duct D having a wall W. The off-gas is scrubbed in unit B to give the cleaned air stream 5 which is e.g. vented, and a liquid urea-containing purge stream 6. The purge stream 6 containing urea is disposed of for instance by recycle to the urea plant. In the invention, the duct D is provided with a heating and/or insulation element E for preventing heat loss in at least part of the wall W of the duct D. The heating and/or insulation element E is e.g. tracing, provided over at least part of the wall, e.g. using electric heating or a heating fluid 7, such as steam or condensate. Urea deposition on wall W by isocyanic acid condensation and reaction thereof with ammonia in off-gas stream 4 is avoided by the heating and/or insulation element E.

Figure 3:
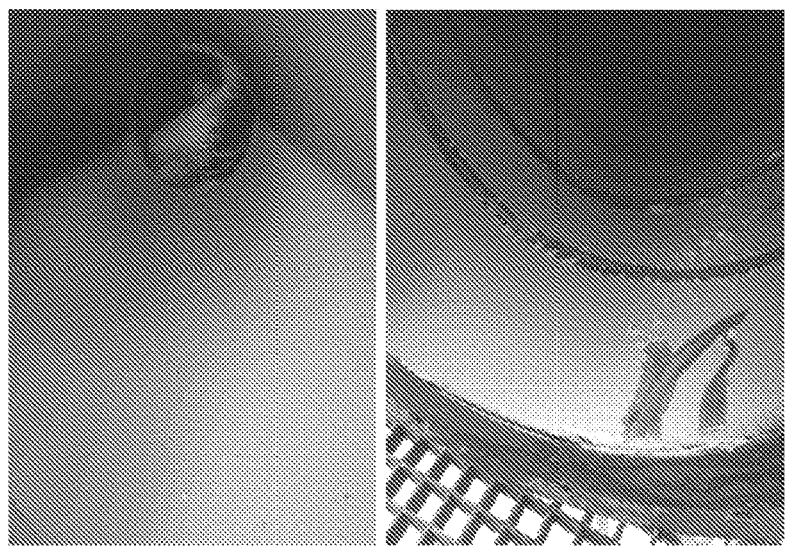
FIG. 3 shows photographs of a duct between a prilling tower and a scrubber according to the invention, wherein the duct is thermally insulated.

FIG. 3 shows two photographs of a duct between a prilling tower and a scrubber according to the invention, wherein the duct is thermally insulated. The photographs were taken after 2 weeks of discontinuous operation of a pilot plant. The deposited solids are located only at the bottom part of the duct and are attributed to settling of urea particles (urea dust) by gravity. In contrast to FIG. 1, no large clogs of solid deposits are formed. The settled particles do not adhere to the wall and are easily removed as shown in the right panel of FIG. 3.

Example 1

In comparative plant 1, the scrubber was connected by a duct to a finishing section. The duct was not thermally insulated or heated. Depending on the outside temperature, the amount of fines <1 μm was 10-70 wt. %, with higher amounts of fines at colder temperatures. Furthermore, at lower temperatures, the gas stream at the end of the duct contained less isocyanate and less ammonia at lower temperatures. The gas stream contained 10-90 mg isocyanate/Nm$^3$ at the inlet of the scrubber, depending on the temperature at the inlet of the scrubber, which was in the range of 44 to 63° C.

For an inventive plant 2 with a thermally insulated duct between the finishing section (a prilling tower) and the scrubber, the amount of fines <1 μm was normally 5 to 25%. The amount was not correlated with outside ambient temperature. The gas stream contained 100 to 220 mg isocyanate/Nm$^3$ at the inlet of the scrubber, and was not correlated to the temperature of the off-gas at the inlet of the scrubber, i.e. the off-gas temperature downstream of the prilling tower and at the downstream end of the duct, which was in the range 58 to 70° C. and which was varied with the outside ambient temperature.

This indicates that isocyanate and ammonia react at lower temperatures in the non-insulated duct and that also submicron urea dust is formed. In the inventive plant 2, this is avoided.

The invention claimed is:

1. A finishing process for urea-comprising material comprising:
    subjecting a urea-comprising liquid stream to solidification in a urea finishing section, yielding a solid urea-comprising product and an off-gas stream comprising air, urea dust and ammonia,
    transporting said off-gas stream from an outlet of said urea finishing section to an off-gas treatment section through a conduit having a wall, wherein said off-gas has a temperature $T_1$ at said outlet,
    subjecting said off-gas stream to a treatment to remove at least part of said urea dust and/or ammonia from said air in said treatment section, and
    maintaining a temperature of said wall of said conduit higher than $T_{w,min}$, in at least one bend of the conduit, in at least one section where the diameter of the conduit changes and/or over at least 10%, of the length of the conduit, wherein $T_{w,min}=T_1-50°$ C.

2. The finishing process of claim 1, wherein said wall of said conduit is provided with thermal insulation material and with heating elements.

3. The finishing process of claim 1, wherein the temperature of the wall is maintained at a temperature equal to or higher than $T_1$.

4. The finishing process of claim 1, wherein the temperature of the off-gas stream in a zone less than 2 cm from said wall is higher than 60° C., preferably higher than 65° C., even more preferably higher than 70° C.

5. The finishing process of claim 1, wherein the difference in temperature between the gas stream near the wall of the conduit and the gas stream in the centre in cross-section of the conduit, at the same position in the length of the conduit, is less than 10° C., preferably less than 5° C.

6. The finishing process of claim 1, comprising maintaining the wall at a temperature of at least 60° C.

7. The finishing process of claim 1, wherein said solid urea-comprising product comprises urea particles, urea ammonium nitrate (UAN) particles, or urea ammonium sulfate (UAS) particles.

8. The finishing process of claim 1, wherein said solidification comprises prilling of urea-containing melt to give urea prills.

9. The finishing process of claim 1, comprising
    prilling urea in a forced draft urea prilling tower using cooling air and using a blower and/or fan, wherein the prilling tower has an outlet for off-gas at the top of said tower, wherein said off-gas has a temperature $T_1$ at said outlet,
    subjecting said off-gas to dust scrubbing and optionally to acid scrubbing in an off-gas treatment section having an inlet for off-gas at 0 to 20 m elevation above ground level,
    supplying off-gas from said outlet at said top of the urea prilling tower to said inlet of said off-gas treatment section, and
    maintaining a temperature of said wall of said conduit higher than $T_{w,min}=T_1-10°$ C.

10. A plant for finishing urea-comprising material, wherein the plant comprises
    a finishing section for solidifying a urea-containing liquid stream,
    an off-gas treatment section, and
    a conduit for off-gas from an outlet of said finishing section to an inlet of said treatment section, wherein said conduit comprises a wall,
and wherein at least parts or all of said conduit are provided with thermal insulation and/or with one or more heating elements for maintaining a minimum temperature of said wall, wherein said thermal insulation and said one or more heating elements are configured for maintaining a temperature of said wall of said conduit higher than $T_{w,min}$, in at least one bend of the conduit, in at least one section where the diameter of the conduit changes and/or over at least 10%, of the length of the conduit, wherein $T_{w,min}=T_1-50°$ C., wherein $T_1$ is the temperature of said off-gas at said outlet.

11. The plant of claim 10, wherein said conduit is provided with thermal insulation material and with heating elements, wherein the heating elements comprise electric tracing and/or steam tracing.

12. The plant of claim 10, wherein said finishing section is a urea prilling tower, and wherein the inlet for off-gas of said treatment section is at 0 to 20 m elevation above ground level.

13. The plant of claim 10, wherein the conduit is provided with thermal insulation material having a thermal conductivity of less than 1.0 W/(m·K)) and having a thickness of at least 10 mm, preferably wherein the conduit is provided with thermal insulation material comprising one or more materials selected from the group of a polymeric material, a fibre based material, and an inorganic non-metal material.

14. The finishing process of claim 4, wherein the temperature of the off-gas stream in a zone less than 2 cm from said wall is higher than 65° C.

15. The finishing process of claim 4, wherein the temperature of the off-gas stream in a zone less than 2 cm from said wall is higher than 70° C.

16. The finishing process of claim 5, wherein the difference in temperature between the gas stream near the wall of the conduit and the gas stream in the centre in cross-section of the conduit, at the same position in the length of the conduit, is less than 5° C.

17. The plant of claim 13, wherein the conduit is provided with thermal insulation material having a thermal conductivity of less than 1.0 W/(m·K)) and having a thickness of at least 10 mm, wherein the conduit is provided with thermal insulation material comprising one or more materials selected from the group of a polymeric material, a fibre based material, and an inorganic non-metal material.

18. The finishing process of claim 1, wherein said conduit has a length and wherein a temperature of said wall of said conduit higher than $T_{w,min}$ is maintained over at least 50% of the length of the conduit.

19. The finishing process of claim 1 wherein said conduit has a length and wherein a temperature of said wall of said conduit higher than $T_{w,min}$ is maintained over at least 90% of the length of the conduit.

20. The plant of claim 10, wherein said conduit has a length and wherein said thermal insulation and said one or more heating elements are configured for maintaining a temperature of said wall of said conduit higher than $T_{w,min}$ over at least 50% of the length of the conduit.

21. The plant of claim 10, wherein said conduit has a length and wherein said thermal insulation and said one or more heating elements are configured for maintaining a temperature of said wall of said conduit higher than $T_{w,min}$ over at least 90% of the length of the conduit.

\* \* \* \* \*